United States Patent [19]

Buchwald et al.

[11] Patent Number: 5,442,119
[45] Date of Patent: Aug. 15, 1995

[54] CATALYTIC ASYMMETRIC REDUCTION OF TRISUBSTITUTED OLEFINS

[75] Inventors: Stephen L. Buchwald, Somerville, Mass.; Richard D. Broene, Brunswick, Me.

[73] Assignee: Massachusetts Institute of Technology, Cambridge, Mass.

[21] Appl. No.: 90,338

[22] Filed: Jul. 12, 1993

Related U.S. Application Data

[63] Continuation-in-part of Ser. No. 792,229, Nov. 14, 1991, Pat. No. 5,292,893, which is a continuation-in-part of Ser. No. 698,940, May 13, 1991, abandoned, which is a continuation-in-part of Ser. No. 616,892, Nov. 21, 1990, Pat. No. 5,286,878.

[51] Int. Cl.$^6$ .................. C07C 211/27; C07C 43/20; C07C 43/205; C07C 25/02; C07C 5/11
[52] U.S. Cl. ..................... 564/374; 564/343; 564/391; 568/630; 570/250; 585/266
[58] Field of Search ............... 564/356, 357, 358, 343, 564/374, 391; 568/630; 570/250; 585/266

[56] References Cited

PUBLICATIONS

*Catalytic Asymmetric Synthesis*, Iwao Ojima, Ed., Ch. 1, pp. 1–39 (1993, VCH Publishers, Inc.).
"Complexes with Chiral Alkylcuclopentadienyl Ligands for Homogenous Catalytic Asymmetric Hydrogenation of 2-Phenyl-1-butene", Cesarroti et al., *Agnew. Chem. Int. Ed. Engl.* (1979) 18:779–780.
"Syntheses of [Ethylene-1,2bis($\eta^5$-4,5,6,7-tetrahydro-1-indenyl)]zirconium and hafnium Hydride Complexes. Improved Syntheses of the Corresponding Dichlorides", Grossman et al., *Organmetallics*, (1991) 10:1501–1505.
"Chiral Metal Complexes as Discriminating Molecular Catalysts", Noyori, *Science* (1990), 248:1194–1199.
"Chiral Organolanthanide Complexes for Enantioselective Olefin Hydrogenation", Conticello et al., *J. Am. Chem. Soc.* (1992) 114:2761–2762.
"Recent Advances in Catalytic Asymmetric Reactions Promoted By Transition Metal Complexes," Ojima et al., *Tetrahedron* (1989) vol. 45, No. 22:6901–6939.
"Synthesis and Asymmetric Reactivity of Enantiomerically Pure Cyclopentadienylmetal Complexes Derived from the Chiral Pool", Halterman, et al., II *Organometallics* (1988), vol. 7, No. 4:883–892.
"A Designed Enantiomerically Pure, Fused Cyclopentadienyl Ligand with C$_2$ Symmetry: Synthesis and Use in Anantioselective Titanocene–Catalyzed Hydrogenations of Alkenes", Halterman et al., I *J. Am. Chem. Soc.* (1987) 109:8105–8107.
Broene et al, *J. Am. Chem. Soc.*, vol. 115, pp. 12569–12570 (1993).
Takaya et al, *J. Am. Chem. Soc.*, vol. 109, pp. 1596–1597 (1987).

*Primary Examiner*—Floyd D. Higel
*Attorney, Agent, or Firm*—Thomas J. Engellenner; William C. Geary, III; Lahive & Cockfield

[57] ABSTRACT

A catalytic asymmetric reduction process, which, by hydrogenating trisubstituted olefins, yields a corresponding organic compound having a high level of enantiomeric purity is disclosed. The reduction process utilizes a chiral metal catalyst that includes a metal or metal complex that is selected from groups 3, 4, 5, or 6, lanthanides and actinides. Moreover, the process uses hydrogen as the stoichiometric reducing agent and may be carried out at pressures ranging from about 1 to 200 atmospheres.

8 Claims, No Drawings

CATALYTIC ASYMMETRIC REDUCTION OF TRISUBSTITUTED OLEFINS

GOVERNMENT SUPPORT

The U.S. Government has rights in this invention pursuant to NIH Grant Number GM 46059.

REFERENCE TO RELATED APPLICATIONS

This is a continuation-in-part of U.S. patent application Ser. No. 792,229, filed Nov. 14, 1991, (now U.S. Pat. No. 5,292,893) entitled "Catalytic Asymmetric Reduction of Imines and Oximes", which is a continuation-in-part of abandoned U.S. patent application Ser. No. 698,940, filed May 13, 1991, (now abandoned) entitled "Catalytic Asymmetric Reduction of Imines and Oximes", which is a continuation-in-part application of U.S. patent application Ser. No. 616,892, filed Nov. 21, 1990, (now U.S. Pat. No. 5,286,878) entitled "Catalytic Reduction of Organic Carbonyls".

BACKGROUND OF THE INVENTION

The present invention relates to processes for the catalytic asymmetric reduction of trisubstituted olefins.

Processes that economically and efficiently produce enantiomerically enriched organic compounds are of great interest since these compounds are widely used as pharmaceuticals and specialty chemicals. More specifically, reactions that reduce trisubstituted olefins to yield enantiomerically enriched products are commercially quite significant as they can be used in the large scale preparation of pharmaceuticals and specialty chemicals. Thus, the effectiveness and economy of such reduction reactions are important considerations.

Currently utilized methods of producing enantiomerically enriched products by hydrogenation of trisubstituted olefins rely upon the use of expensive late transition metal catalysts such as rhodium and ruthenium. See, Noyori, R. Science 1990, 248, 1194–1199; Ojima, I., et al Tetrahedron 1989, 45, 6901–39. In addition, many types of trisubstituted olefins cannot be efficiently converted, by hydrogenation, to enantiomerically enriched organic compounds using the catalyst systems currently available.

Accordingly, it would be advantageous to provide more economical and efficient processes for asymmetrically reducing trisubstituted olefins.

It is thus an object of the invention to provide more economical and effective processes for the asymmetric reduction of trisubstituted olefins. Another object is to provide an effective process to obtain from trisubstituted olefins enantiomerically enriched compounds such as hydrocarbons and functionalized hydrocarbons. Other objects will be apparent upon reading the disclosure that follows.

SUMMARY OF THE INVENTION

The disclosure of the related parent applications, U.S. patent application Ser. No. 792,229, filed Nov. 14, 1991 entitled "Catalytic Asymmetric Reduction of Imines and Oximes", U.S. patent application Ser. No. 698,940, filed May 13, 1991, entitled "Catalytic Asymmetric Reduction of Imines and Oximes", and U.S. patent application Ser. No. 616,892, filed Nov. 21, 1990, entitled "Catalytic Reduction of Organic: Carbonyls", are all hereby incorporated by reference.

Unless otherwise clear from its context, the term "catalyst" is used interchangeably herein to refer both to the metal complexes or precatalysts before their activation as catalytic species, and to the active catalytic species themselves.

The invention provides an effective process for the catalytic asymmetric reduction of trisubstituted olefins to yield chiral organic compounds enriched in one enantiomer. The term trisubstituted olefin refers to a molecule which contains a carbon-carbon double bond with three substituents that are neither hydrogen nor deuterium. Trisubstituted olefins are represented by the general structural formulas shown below.

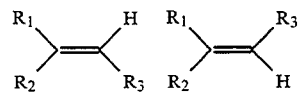

Generally, the process of the invention involves first generating an active species of an effective, optically active reduction catalyst which is used in the reaction. The substrate is then reacted with the active catalyst at a temperature range of 25° C. to 100° C. and at pressures ranging from 1 to 200 atmospheres of hydrogen. When the reaction is complete one need only perform conventional separation and purification techniques to yield the desired enantiomerically enriched end product.

Formation of the active catalyst can be effected by dissolving the precatalyst in an organic solvent in an inert atmosphere or in an atmosphere of hydrogen. Thereafter, the precatalyst/solvent mixture can be subjected to between 1 and 2 equivalents, relative to the, amount of precatalyst, of an alkylating or reducing agent. The reaction mixture can then be placed in an atmosphere of hydrogen gas at a pressure between 1 and 200 atmospheres. The reaction can then be conducted using hydrogen alone, or in combination with a substoichiometric amount of a silane relative to the amount of substrate.

The process of the invention preferably is carried out where hydrogen serves as the reducing agent. In such an embodiment the active catalytic species is generated under an inert gas such as argon or nitrogen, or under an atmosphere of hydrogen. Thereafter, a substoichiometric quantity of a silane compound (relative to the substrate) may optionally be added. The reduction reaction takes place in an atmosphere of hydrogen which is present in excess and serves as the stoichiometric reductant.

In another embodiment no alkylation is necessary. The reaction is able to proceed by mixing together, in a hydrogen atmosphere, in a suitable reaction vessel, the precatalyst, the desired substrate, and, optionally, a substoichiometric quantity, relative to substrate, of a silane .compound.

The reduction of trisubstituted olefins by this reaction yields, after quenching of the catalyst, a crude end product in a more reduced form than the starting compound. The end product may then be purified by known techniques.

DETAILED DESCRIPTION OF THE INVENTION

The process of the invention can be used to effect the catalytic asymmetric reduction of trisubstituted olefins to produce corresponding organic compounds that are enriched in one enantiomer. The catalyst preferably is enriched in one enantiomer. Generally, an enantiomerically enriched catalyst is one which has more than 50 percent of one enantiomer. More specifically, an enantiomerically enriched catalyst is one which has greater than 80%, and most preferably greater than 90% of one enantiomer.

The trisubstituted olefin substrates to which the invention is directed are represented by the formulas shown below.

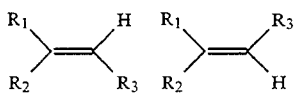

where $R_1$, $R_2$ and $R_3$ are neither hydrogen nor deuterium, and where $R_1$ and $R_2$ are different. $R_1$, $R_2$ and $R_3$ can be selected from among a variety of functional groups.

The trisubstituted olefin substrates that are useful with the processes of the present invention are converted to compounds in a more reduced state of having general formula $(H)(R_1)(R_2)CCH_2R_3$, where $R_1$ is not the same as $R_2$ and $R_1$, $R_2$ and $R_3$ are neither H nor D. $R_1$ and $R_2$ may be part of a ring system, and $R_2$ and $R_3$ may be part of a ring system. Further, $R_1$, $R_2$ and $R_3$ may be any combination of substituted and/or unsubstituted alkyl, aryl, alkenyl, alkynyl, or heteroaromatic groups, and may be $N(R')R''$, where $R'$ and $R''$ are aryl and/or alkyl groups, substituted and/or unsubstituted, $SR'$, where $R'$ is an aryl or alkyl group, substituted or unsubstituted, $OR'$, where $R'$ is an aryl or alkyl group, substituted or unsubstituted, and $Si(R')(R'')(R''')$, where $R'$, $R''$, $R'''$ are alkyl or aryl groups, substituted or unsubstituted. $R_1$, $R_2$ or $R_3$ also may be a halogen and/or a COX group, where X is $OR'$, where $R'$ is an aryl or alkyl group, substituted or unsubstituted, X is $N(R')R''$, where $R'$ and $R''$ are aryl and/or alkyl groups, substituted or unsubstituted, or X is an alkyl or an aryl group, substituted or unsubstituted.

The basic steps of the invention involve first generating an active species of an effective, optically active catalyst. This can be accomplished by dispensing a suitable optically active precatalyst in an organic solvent such as tetrahydrofuran, ether, toluene, benzene, hexane, or the like. Preferably, this mixture is maintained in an atmosphere of an inert gas, such as argon or nitrogen, or in an atmosphere of hydrogen gas. In some instances, especially where certain titanium-containing catalysts are used, as explained below in more detail, the precatalyst may be activated by dissolving the catalyst in a solvent, followed by the addition of an alkylating agent. Thereafter, a substoichiometric quantity of a silane compound, relative to the substrate, may optionally be added to the reaction mixture. The desired substrate is added to the mixture and the reactants may be transferred to a reaction vessel that is able to be charged with hydrogen at ambient or elevated pressures.

The reduction reactions of the present invention preferably use hydrogen as the stoichiometric reducing agent. The hydrogen reducing agent can be used alone, or it can be used in combination with a substoichiometric amount, relative to the substrate, of a silane compound.

Where the reaction is to be conducted using hydrogen as the reducing agent at high pressure, the precatalyst/solvent mixture is, optionally, subjected to vacuum to remove the inert gas, and hydrogen gas can then be added to the reactor vessel. The reactor vessel contents can then be cooled to about 0° C. and allowed to equilibrate. Thereafter, an alkylating agent is generally added to the reactor vessel. Optionally, a silane compound can then be added at a substoichiometric amount relative to the substrate. The desired substrate is then added and the reaction vessel can be sealed and placed in a dry box. The vessel is then transferred to a high pressure reactor (such as a Parr ® high pressure reactor) and it is removed from the dry box. The reactor is then charged with hydrogen at a desired pressure and the reaction commences upon heating to between 25°–100° C. The reaction can be conducted in hydrogen at a pressure ranging from 1 atmosphere to over 200 atmospheres.

The reaction typically requires from 1 to 200 hours to complete. Once completed, the reaction vessel is cooled to room temperature, vented and opened to air to quench the catalyst. Well known separation and purification techniques can then be utilized to obtain the end product, which is enriched in one enantiomer.

The present reduction reaction preferably requires between about 0.1–40% by mole of catalyst relative to the substrate, and more preferably, between about 5–10% by mole of catalyst relative to the substrate.

A variety of precatalysts can be used effectively in the reduction reactions of the present invention. Exemplary precatalysts broadly include those that are chiral, either by virtue of the chirality of a ligand or by virtue of chirality at the metal center. Exemplary precatalysts are chiral precatalysts having the general formulas:

$$M(L)(L')(L'') \tag{1}$$

$$M(L)(L')(L'')(L''') \tag{2}$$

$$M(L)(L')(L'')(L''')(L^{iv}) \tag{3}$$

$$M(L)(L')(L'')(L''')(L^{iv})(L^v) \tag{4}$$

where M is a group 3, 4, 5 or 6 metal, a lanthanide, or an actinide and where L, L', L'', and L''', $L^{iv}$ and $L^v$, independently, can be some combination of H, an alkyl group, an aryl group, a cyclopentadienyl group, $Si(R)(R')(R'')$, a halogen, —OR, —SR, —NR(R'),or PR(R')(R''), where R, R' and R'' may be H, an alkyl, aryl, or silyl group and may be different or the same. A cyclopentadienyl group (designated "Cp") is represented by the formula

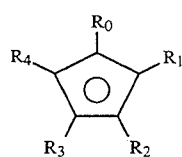

where $R_0$, $R_1$, $R_2$, $R_3$, and $R_4$ may be hydrogen, alkyl, aryl, $Si(R)(R')(R'')$, a halogen, —OR, —SR, —NR(R'), PR(R')(R''), or —PR(R'), where R, R' and R'' may be H, an alkyl, aryl, or silyl group and may be different or the same. Examples of group 3, 4, 5 or 6 metals which may be useful with the present invention include titanium, vanadium, niobium, and chromium. Examples of useful lanthanides include yttrium, scandium, lanthanium, samarium, ytterbium, and lutetium. Examples of useful actinides include thorium and uranium. Titanium, however, is the most preferred metal.

A preferred precatalyst, which is particularly useful in conducting catalytic asymmetric reduction reactions is generally represented by the formula $$Y_2MX_n$$

where Y represents a substituted cyclopentadienyl or indenyl group or where $Y_2$ represents a substituted bis-cyclopentadienyl or bis-indenyl group; M represents a group 3, 4, 5, 6 metal, a lanthanide or an actinide; X represents groups including halides, alkoxides, amides, sulfides, phosphines, alkyls, aryls, hydrides, and mono-, di-, and tri-substituted silyls, and carbon monoxide; and $X_2$ can be an $\eta^2$-olefin or an $\eta^2$-alkyne; and n is an integer from 1 to 4. In a preferred embodiment $Y_2$ is ethylene-1,2-bis($\eta^5$-4,5,6,7-tetrahydro-1-indenyl) and $X_2$ represents 1,1'-binaphth-2,2'-diolate.

Precatalysts having the ethylene-1,2-bis($\eta^5$-4,5,6,7-tetrahydro-1-indenyl backbone are referred to herein as "BIE" catalysts. Specific preferred catalysts for asymmetric reduction include (R,R)-ethylene-1,2-bis ($\eta^5$-4,5,6,7-tetrahydro-1-indenyl)titanium-(R)-1,1'-binaphth-2,2'-diolate; (S,S)-ethylene-1,2-bis($\eta^5$-4,5,6,7-tetrahydro-1-indenyl)titanium-(S)-1,1'-binaphth-2,2'-diolate; (R,R)-1,1'-Trimethylenebis($\eta^5$-3-tertbutylcyclopentadienyl)-titanium(IV) dichloride; (S,S)-1,1'-Trimethylenebis($\eta^5$-3-tertbutylcyclopentadienyl)-titanium(IV) dichloride; (R,R)-Ethylene-bis($\eta^5$-4,5,6,7-tetrahydro-1-indenyl)titanium(IV) dichloride; (S,S)-Ethylene-bis($\eta^5$-4,5,6,7-tetrahydro-1-indenyl)titanium(IV) dichloride; (R,R)-2,2'-Bis(1-indenylmethyl)1-1'-binaphthyl titanium(IV) dichloride; (S,S)-2,2'-Bis(1-indenylmethyl)1-1'-binaphthyl titanium(IV) dichloride; (R,R)-Ethylene-bis($\eta^5$-4,5,6,7-tetrahydro-1-indenyl) dimethyl titanium(IV); and (S,S)-Ethylene-bis($\eta^5$-4,5,6,7-tetrahydro-1-indenyl) dimethyl titanium(IV).

The BIE-type precatalysts useful with the catalytic asymmetric reduction reactions of the invention are enriched in one enantiomer of the molecule. Enantiomeric enrichment, as the term is used herein, requires more than 50% of and enantiomer, and more preferably requires more than 80% of one enantiomer. In a preferred embodiment, an enantiomerically enriched catalyst has more than 90% of one enantiomer.

Other preferred catalysts include metal alkoxides and metal aryloxides such as titanium alkoxides and titanium (IV) aryloxides. Specific examples of such catalysts include (R,R)-2,2'-Dimethyl-α,α,α',α'-tetrakis(β-napthyl)-1,3-dioxolan-4,5-dimethoxy diisopropoxy titanium(IV) and (S,S)-2,2'-Dimethyl-α,α,α',α'-tetrakis(β-napthyl)-1,3-dioxolan-4,5-dimethoxy diisopropoxy titanium(IV).

Precatalysts, including BIE catalysts, may need to be activated by reaction with an alkylating agent or reducing agent, preferably in an organic solvent. Suitable alkylating agents are known to those skilled in the art and generally include organometallic compounds. Examples of such compounds include alkylmagnesium halides, alkyllithium compounds, alkyl aluminum compounds and boron, aluminum, or other metal alkyls or metal hydrides. Particularly preferred alkylating agents include n-pentylmagnesium bromide and n-butyllithium. Preferred reducing agents include sodium bis(2-methoxyethoxy) aluminum hydride (Red Al ®). Preferably, about 100 to 200% by mole of the alkylating agent (relative to precatalyst) should be reacted with the precatalyst in order for activation to occur. The activation of such catalysts by reaction with an alkylating agent is further described and illustrated in the examples.

Metal alkoxide and metal aryloxide catalysts may be air stable, and may be self-activating (i.e., require no alkylation step), or may be activated by the presence of a silane compound.

The catalysts useful in this invention may be active as electronically neutral molecules, anions or cations.

One skilled in the art will appreciate that a variety of solvents may be used with these catalysts. One general requirement of a suitable solvent is that the catalyst must be completely or partially soluble within the solvent. Complete solubility is not required as there need only be enough catalyst present in the solution to facilitate a reaction. Exemplary solvents include tetrahydrofuran, toluene, benzene, hexane, ether and the like.

As noted above, hydrogen is the reducing reagent used in the present catalytic asymmetric reduction processes. Hydrogen may be used alone or in the presence of a substoichiometric amount (relative to the substrate) of a silane compound. A suitable silane compound is one that possesses a silicon-hydrogen bond. Exemplary silane compounds which may be used in these processes (with a hydrogen reducing agent) are represented by the formulas shown below.

$$R(R')SiH_2 \qquad (5)$$

$$RSiH_3 \qquad (6)$$

$$RO(R'O)SiH_2 \qquad (7)$$

$$(RO)(R'O)(R''O)SiH \qquad (8)$$

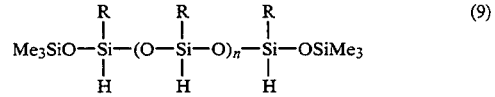

$$(9)$$

where R, R' and R" represent alkyl, aryl or hydride groups and may be the same or different. Specific examples of suitable silane reducing reagents include silane, diphenylsilane, phenylsilane, diethylsilane, dimethylsilane, triethoxysilane, trimethoxysilane, and poly(methylhydrosiloxane).

The silane compound, when used in a substoichiometric amount, can be present at about 0.1 to 5 equivalents, and more preferably 0.1–2.5 equivalents, relative to the catalyst.

One aspect of the invention, as noted above, involves the catalytic asymmetric reduction of trisubstituted olefins to yield organic compounds having a high degree of enantiomeric purity. The desired trisubstituted olefin substrate can be reduced to yield a product enriched in one enantiomer, using a suitable catalyst of the type described above, which is enriched in one enantiomer. A preferred catalyst is one which is enriched in (R,R)-ethylene-1,2-bis($\eta^5$-4,5,6,7-tetrahydro-1-indenyl)-titanium-(R)-1,1-binaphth-2,2'-diolate. Another preferred catalyst is one which is enriched in (S,S)-ethylene-1,2-bis($\eta^5$-4,5,6,7-tetrahydro-1-indenyl)titanium-(S)-1,1-binaphth-2,2'-diolate. Preferably, these catalysts contain at least about 80% of the (R, R, R) or (S,S,S) enantiomers, respectively.

The degree of enantiomeric excess ("ee") for the reaction product depends on a number of factors including the enantiomeric purity of the catalyst, the specific trisubstituted olefin substrate being reduced, and the reaction conditions. Many reactions conducted according to the process of the present invention yield end products having relatively high enantiomeric excesses. In some instances, the ee exceeds 90%.

The asymmetric reduction of trisubstituted olefin substrates is further described and illustrated by the examples that follow.

EXAMPLES

In the examples that follow all reactions were conducted under an atmosphere of argon, nitrogen or hydrogen using standard Schlenk and glove box techniques. Hydrogenation reactions were conducted in a glass pressure reaction vessel (purchased from Aerosol Lab Equipment, Walton, N.Y. 13856) or in a Parr® Model 4751 high pressure reaction vessel. The enantiomeric excess values of the products were determined by HPLC analysis using a Chiralcel OD column, unless otherwise noted. HPLC chromatograms were compared with those of the racemic alkanes.

EXAMPLE 1

Reduction of E-3-(4-methoxyphenyl)-2-methyl-1-methoxy-2-propene to 3-(4-methoxyphenyl)-2-methyl-1-methoxypropane In a dry sealable Schlenk flask under an argon atmosphere 0.0573 g (0.096 mmol) of (S,S)-ethylene-1,2-bis($\eta^5$-4,5,6,7-tetrahydro-1-indenyl)titanium (S)-1,1'-binaphth-2,2'-diolate was dissolved in THF (10 mL). The vessel was degassed by exposure to vacuum (2 x ~10 sec) and put under an atmosphere of hydrogen and subsequently cooled to 0° C. in an ice water bath. After equilibration, a solution of n-butyllithium (0.123 mL, 1.52M in hexanes, 0.187 mmol, 1.95 equiv) was added and the mixture was allowed to stir for 10 min. Phenylsilane (0.030 mL, 0.236 mmol, 2.4 equiv) was then added followed, after 5 minutes, by E-3-(4-methoxyphenyl)-2-methyl-1-methoxy-2-propene (0.345 g, 1.92 mmol, 20 equiv). The flask was sealed and the solution moved into a dry box and transferred to a Parr® high pressure reaction vessel containing a magnetic stir bar. The vessel was sealed and moved to a fume hood where it was charged to ~2000 psig with hydrogen and placed in an oil bath at 65° C. The reaction mixture was allowed to stir for 43.5 h. The vessel was cooled to room temperature, vented and opened to air. The reaction mixture was worked up by partitioning between diethyl ether/hexane (¼) and water and separating the layers. The aqueous layer was extracted twice with ether/hexane and the combined organic layers were dried over MgSO₄. The solvent was removed in vacuo and the residue distilled at reduced pressure to yield 0.225 g (1.42 mmol, 74%) of 3-(4-methoxyphenyl)-2-methyl-1-methoxypropane which had an ee of 92.7%.

EXAMPLE 2

Reduction of E-1,2-diphenylpropene to R(-)-1,2-Diphenylpropane

In a dry sealable Schlenk flask under an argon atmosphere 0.102 g (0.171 mmol) (S,S)-ethylene-1,2-bis($\eta^5$-4,5,6,7-tetrahydro-1-indenyl)titanium (S)-1,1'-binaphth-2,2'-diolate was dissolved in THF (16 mL). The vessel was degassed by exposure to vacuum (2 x ~10 sec), put under an atmosphere of hydrogen and subsequently cooled to 0° C. in an ice water bath. After equilibration, a solution of n-butyllithium (0.211 mL, 1.58M in hexanes, 0.333 mmol, 1.95 equiv) was added and the mixture was allowed to stir for 10 min at which point it was a green color. Phenylsilane (0.055 mL, 0.432 mmol 2.4 equiv) was then added. The flask was sealed and the solution moved into a dry box and transferred to a Parr® high pressure reaction vessel containing a magnetic stir bar and E-1,2-diphenylpropene (0.66 g, 3.36 mmol, 20 equiv). The pressure vessel was sealed and moved to a fume hood where it was charged to 1500 psig with hydrogen and placed in an oil bath at 65° C. The reaction mixture was allowed to stir for 65 h. The vessel was cooled to room temperature, vented and opened to air. The reaction mixture was worked up by partitioning between diethyl ether/hexane (¼) and water and separating the layers. The organic extract was concentrated and was run through a 50 mL plug of silica gel to yield 0.628 g (3.2 mmol, 94%) of R(-)-1,2-Diphenylpropane. The ee was found, polarimetrically, to be greater than 99%.

EXAMPLE 3

Reduction of 6-methoxy-1-methyl-3,4-dihydronaphthalene to 6-methoxy-1-methyl-1,2,3,4-tetrahydronaphthalene In a dry sealable Schlenk flask under an argon atmosphere 0.0592 g (0.099 mmol) (S,S)-ethylene-1,2-bis($\eta^5$-4,5,6,7-tetrahydro-1-indenyl)titanium (S)-1,1'-binaphth-2,2'-diolate was dissolved in THF (10 mL). The vessel was degassed by exposure to vacuum (2 x ~10 sec), put under an atmosphere of hydrogen and subsequently cooled to 0° C. in an ice water bath. After equilibration, a solution of n-butyllithium (0.122 mL, 1.58M in hexanes, 0.193 mmol, 1.95 equiv) was added and the mixture was allowed to stir for 10 min. Phenylsilane (0.03 1 mL, 0.243 mmol, 2.5 equiv) and 0.378 g (2.19 mmol, 22 equiv) 6-methoxy-1-methyl-3,4-dihydronaphthalene were then added. The flask was sealed and the solution moved into a dry box and transferred to a Parr® high pressure reaction vessel containing a magnetic stir bar. The pressure vessel was sealed and moved to a fume hood where it was charged to 1800 psig with hydrogen and placed in an oil bath at 68° C. The reaction mixture was allowed to stir for 132 h. The vessel was cooled to room temperature, vented and opened to air. The reaction mixture was worked up by partitioning between diethyl ether hexane (¼) and water and separating the layers. The organic extract was concentrated and chromatographed on 50 mL silica gel to yield 0.268 g (1.54 mmol, 70%) of 6-methoxy-1-methyl-1,2,3,4-tetrahydronaphthalene with an ee of 94.7%.

EXAMPLE 4

Reduction of 1-methyl-3,4-dihydronaphthalene to 1-methyl-1,2,3,4-tetrahydronaphthalene In a dry sealable Schlenk flask under an argon atmosphere 0.059 g (0.099 mmol) (S,S)-ethylene-1,2-bis($\eta^5$-4,5,6,7-tetrahydro-1-indenyl)titanium (S)-1,1'-binaphth-2,2'-diolate was dissolved in THF (10 mL). The vessel was degassed by exposure to vacuum (2 x ~10 sec), put under an atmosphere of hydrogen and subsequently cooled to 0° C. in an ice water bath. After equilibration, a solution of n-butyllithium (0.125 mL, 1.58M in hexanes, 0.196 mmol, 1.96 equiv) was added and the mixture was allowed to stir for 10 min. Phenylsilane (0.033 mL, 0.259 mmol, 2.6 equiv) and 0.273 g (1.87 mmol, 19 equiv) 1-methyl-3,4-dihydronaphthalene were then added. The flask was sealed and the solution moved into a dry box and transferred to a Parr® high pressure reaction vessel containing a magnetic stir bar. The pressure vessel was sealed and moved to a fume hood where it was charged to 2150 psig with hydrogen and placed in an oil bath at 65° C. The reaction mixture was allowed to stir for 184 h. The vessel was cooled to room temperature, vented and opened to air. The reaction mixture was worked up by partitioning between diethyl ether/hexane (¼) and water and separating the layers. The organic extract was distilled at reduced pressure to yield 0.195 g (1.31 mmol, 70%) of 1-methyl-1,2,3,4-tetrahydronaphthalene with an ee of 70%, determined polarimetrically.

EXAMPLE 5

Reduction E-2-(4-methoxyphenyl)-2-butene to 2-(4-methoxyphenyl) butane

In a dry sealable Schlenk flask under an argon atmosphere 0.0364 g (0.061 mmol) (S,S)-ethylene-1,2-bis($\eta^5$-4,5,6,7-tetrahydro-1-indenyl)titanium (S)-1,1-binaphth-2,2'-diolate was dissolved in THF (10 mL). The vessel was degassed by exposure to vacuum (2 x ~10 sec), put under an atmosphere of hydrogen and subsequently cooled to 0° C. in an ice water bath. After equilibration, a solution of n-butyllithium (0.075 mL, 1.58M in hexanes, 0.118 mmol, 1.94 equiv) was added and the mixture was allowed to stir for 10 min. Phenylsilane (0.017 mL, 0.133 mmol, 2.4 equiv) and 0.189 g (1.17 mmol, 19.2 equiv) E-2-(4-methoxyphenyl)-2-butene were then added. The flask was sealed and the solution moved into a dry box and transferred to a Parr ® high pressure reaction vessel containing a magnetic stir bar. The pressure vessel was sealed and moved to a fume hood where it was charged to 2100 psig with hydrogen and placed in an oil bath at 69° C. The reaction mixture was allowed to stir for 65 h. The vessel was cooled to room temperature, vented and opened to air. The reaction mixture was worked up by partitioning between diethyl ether/hexane (¼) and water and separating the layers. The organic extract was distilled at reduced pressure to yield 0.1338 (0.811 mmol, 69%) of 2-(4-methoxyphenyl)propane with an ee of 96.2%.

EXAMPLE 6

Reduction of 7-methoxy-2-methyl-3,4-dihydronaphthalene to 7-methoxy-2-methyl-1,2,3,4-tetrahydronaphthalene In a dry sealable Schlenk flask under an argon atmosphere 0.0254 g (0.043 mmol) (S,S)-ethylene-1,2,-bis($\eta^5$-4,5,6,7-tetrahydro-1-indenyl)titanium (S)-1,1'-binaphth-2,2'-diolate was dissolved in THF (5 mL). The vessel was degassed by exposure to vacuum (2 x ~10 sec), put under an atmosphere of hydrogen and subsequently cooled to 0° C. in an ice water bath. After equilibration, a solution of n-butyllithium (0.052 mL, 1.58M in hexanes, 0.083 mmol, 1.91 equiv) was added and the mixture was allowed to stir for 10 min. Phenylsilane (0.016 mL, 0.126 mmol, 2.9 equiv) and 0.130 g (0.756 mmol, 18 equiv) 7-methoxy-2-methyl-3,4-dihydronaphthalene were then added. The flask was sealed and the solution moved into a dry box and transferred to a Parr ® high pressure reaction vessel containing a magnetic stir bar. The pressure vessel was sealed and moved to a fume hood where it was charged to 2150 psig with hydrogen and placed in an oil bath at 70° C. The reaction mixture was allowed to stir for 44 h. The vessel was cooled to room temperature, vented and opened to air. The reaction mixture was worked up by partitioning between diethyl ether/hexane (¼) and water and separating the layers. The organic extract was distilled at reduced pressure to yield 0.097 g (0.557 mmol, 73%) of 7-methoxy-2-methyl-1,2,3,4-tetrahydronaphthalene with an ee of 90.4%.

EXAMPLE 7

Reduction of E-N,N-Dibenzyl-3-phenyl-2-buten-1-amine to N,N-Dibenzyl-3-phenylbutyl-1-amine In a dry sealable Schlenk flask under an argon atmosphere 0.0551 g (0.0922 mmol) (S,S)-ethylene-1,2-bis($\eta^5$-4,5,6,7- tetrahydro-1-indenyl)titanium (S)-1,1'-binaphth-2,2'-diolate was dissolved in THF (10 mL). The vessel was degassed by exposure to vacuum (2 x ~10 sec), put under an atmosphere of hydrogen and subsequently cooled to 0° C. in an ice water bath. After equilibration, a solution of n-butyllithium (0.118 mL, 1.52M in hexanes, 0.179 mmol, 1.95 equiv) was added and the mixture was allowed to stir for 10 min. Phenylsilane (0.029 mL, 0.126 mmol, 2.5 equiv) and 0.550 g (1.68 mmol, 18 equiv) E-N,N-Dibenzyl-3-phenyl-2-buten-1-amine were then added. The flask was sealed and the solution moved into a dry box and transferred to a Parr ® high pressure reaction vessel containing a magnetic stir bar. The pressure vessel was sealed and moved to a fume hood where it was charged to 2000 psig with hydrogen and placed in an oil bath at 65° C. The reaction mixture was allowed to stir for 43 h. The vessel was cooled to room temperature, vented and opened to air. The extraction mixture was treated with 3N HCl (aq); the solid salt isolated from this treatment was neutralized with 15% NaOH and subsequently partitioned between $CH_2Cl_2$ and water. The organic extract was concentrated to yield 0.43 g (1.30 mmol, 74%) of N,N-Dibenzyl-3-phenylbutyl-1-amine which had an ee of 95.3%.

EXAMPLE 8

Reduction of E-N,N-Dibenzyl-3-phenyl-2-buten-1-amine to N,N-Dibenzyl-3-phenylbutylamine with EBTHITiCl2

In a dry sealable Schlenk flask under an argon atmosphere 0.0363 g (0.0948 mmol) (S,S)-ethylene-1,2-bis($\eta^5$-4,5,6,7-tetrahydro-1-indenyl)titanium dichloride was dissolved in THF (10 mL). The vessel was degassed by exposure to vacuum (2x ~10 sec), put under an atmosphere of hydrogen and subsequently cooled to 0° C. in an ice water bath. After equilibration, a solution of n-butyllithium (0.15 mL, 1.22M in hexanes, 0.183 mmol, 1.93 equiv) was added and the mixture was allowed to stir for 10 min. Phenylsilane (0.035 mL, 0.275 mmol, 2.9 equiv) was added, the flask was sealed and the solution moved into a dry box. It was added to a Parr ® high pressure reaction vessel containing a magnetic stir bar and 0.182 g (0.57 mmol, 6 equiv) E-N,N-dibenzyl-3-phenyl-2-buten-1-amine. The pressure vessel was sealed and moved to a fume hood where it was charged to 1950 psig with hydrogen and placed in an oil bath at 65° C. The reaction mixture was allowed to stir for 54 h. The vessel was cooled to room temperature, vented and opened to air. The reaction mixture was worked up by partitioning between diethyl ether/hexane (1:4) and water. The organic extract was concentrated and was chromatographed on 20 mL silica gel with a 1/6 to ⅓ gradient of $CH_2Cl_2$/hexane to yield 0.133 g (0.416 mmol, 73%) of N,N-dibenzyl-3-phenylbutyl-1-amine, which had an ee of 94.4%.

EXAMPLE 9

Reduction of E-1,2-diphenylpropene to R(-)-1,2-Diphenylpropane

In a dry sealable Schlenk flask under an argon atmosphere 0.0599 g (0.100 mmol) (S,S)-ethylene-1,2-bis($\eta^5$-4,5,6,7-tetrahydro-1-indenyl)titanium (S)-1,1'-binapth-2,2'-diolate was dissolved in THF (10 mL). The vessel was degassed by exposure to vacuum (2x ~10 sec), put under an atmosphere of hydrogen and subsequently cooled to 0° C. in an ice water bath. After equilibration, a solution of n-butyllithium (0.128 mL, 1.52M in hexanes, 0.194 mmol, 1.94 equiv) was added and the mixture was allowed to stir for 10 min. Phenylsilane (0.032 mL, 0.25 mmol 2.5 equiv) was then added. The contents were then cannula transferred to a pressure vessel containing a magnetic stir bar and E-1,2-diphenylpropene (0.138 g, 1.96 mmol, 20 equiv) under an atmosphere of hydrogen. The pressure vessel was sealed and moved to a fume hood where it was charged to 89 psig with hydrogen and placed in an oil bath at 65° C. The reaction mixture was allowed to stir for 19 h. The vessel was cooled to room temperature, vented and opened to air. The reaction mixture was worked up by partitioning between diethyl ether/hexane (¼) and water and separating the layers. The organic extract was concentrated and was run through a 50 mL plug of silica gel to yield 0.304g (1.55 mmol, 80%) of R(-)-1,2-Diphenylpropane, with an ee of >99% as determined polarimetrically.

The above examples are intended to be illustrative of the invention and should not be read to limit the invention to the specific reduction reactions provided in the examples. One skilled in the art will readily appreciate that the invention is applicable to a variety of reduction reactions in which the substrate is a trisubstituted olefin, and that a variety of catalysts may be used in these reduction reactions.

What is claimed is:

1. A catalytic asymmetric reduction process, comprising the steps of:
   providing a catalytic amount of an active species of an enantiomerically enriched Chiral catalyst selected from the group consisting of M(L)(L')(L''), M(L)(L')(L'')(L'''), M(L)(L')(L'')(L''')(Liv), and M(L)(L')(L'')(L''')(L$^{iv}$)(L$^v$), where M is a group 3, 4, 5 or 6 metal, a lanthanide or an actinide, and L, L', L'', L''', L$^{iv}$, L$^v$, independently, is some combination of H, alkyl, aryl, Si(R)(R')(R''), halogen, —OR, —SR, or —NR(R'), PR(R')(R''), or a cyclopentadienyl group having the formula

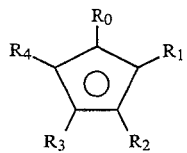

where R, R', and R'' are H, alkyl, aryl, or silyl and may be different or the same, and where $R_0$, $R_1$, $R_2$, $R_3$, and $R_4$ are hydrogen, alkyl, aryl, Si(R)(R')(R''), halogen, —OR, —SR, —NR(R'), PR(R')(R''), or —PR(R') groups in any combination, where R, R', and R'' are as defined above;

reacting a trisubstituted olefin substrate in the presence of hydrogen and the catalyst; and recovering and purifying a reduced organic reaction product having a high level of enantiomeric purity.

2. The process of claim 1 wherein the step of reacting the trisubstituted olefin substrate in the presence of a hydrogen reducing agent and the catalyst is conducted at a hydrogen pressure in the range of I atmosphere to 200 atmospheres.

3. The process of claim 2 wherein before the step of reacting the trisubstituted olefin substrate in the presence of hydrogen and the catalyst, a silane compound is added at a substoichiometric amount relative to the substrate.

4. The process of claim 1 wherein the enantiomerically enriched chiral catalyst is a titanium-containing catalyst selected from the group consisting of L(L')(L'')Ti; L(L')(L'')(L''')Ti; L(L')Ti—X; L(L')(L'')Ti—X; L(L')Ti—X$_2$; L(L')Ti—H; and L(L')(L'')TiH where X is a halogen, and where L, L', L'' and L''', independently, is some combination of H, alkyl, aryl, Si(R)(R')(R''), halogen, —OR, —SR, or —NR(R'), PR(R')(R''),or a cyclopentadienyl group of the structure

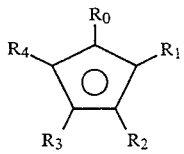

where R, R', and R'' are H, alkyl, aryl, or silyl and may be different or the same, and where $R_0$, $R_1$, $R_2$, $R_3$, and $R_4$ are hydrogen, alkyl, aryl, Si(R)(R')(R''), halogen, —OR, —SR, —NR(R'), PR(R')(R''), or —PR(R') groups in any combination, where R, R', and R'' are as defined above.

5. The process of claim 4 wherein the catalyst is an enantiomerically enriched chiral complex selected from the group consisting of chiral bis(cyclopentadienyl) titanium monohalide complexes; chiral bis(cyclopentadienyl) titanium monoalkoxide complexes; chiral bis(cyclopentadienyl) titanium dihalide complexes; chiral bis(cyclopentadienyl) titanium dialkoxide complexes; and chiral bis(cyclopentadienyl) titanium diaryloxide complexes.

6. The process of claim 5 wherein the catalyst is selected from the group consisting of (R,R)-ethylene-1,2-bis($\eta^5$-4,5,6,7-tetrahydro-1-indenyl) titanium-(R)-1,1-binapth-2,2'-diolate and (S,S)-ethylene-1,2-bis($\eta^5$-4,5,6,7-tetrahydro-1-indenyl)titanium-(S)-1,1-binapth-2,2'-diolate.

7. The process of claim 1 wherein the catalyst is present at about 0.1 to 10% by mole, relative to the substrate.

8. The process of claim 7 wherein the reaction is conducted at a temperature ranging from about 25° to 100° C.

* * * * *

UNITED STATES PATENT AND TRADEMARK OFFICE
CERTIFICATE OF CORRECTION

PATENT NO. : 5,442,119
DATED : August 15, 1995
INVENTOR(S) : Stephen L. Buchwald and Richard D. Broene It is certified that error appears in the above-indentified patent and that said Letters Patent is hereby corrected as shown below:

In column 2, line 55, please replace "silane. compound." with --silane compound.--.

In column 7, line 22, please replace "Reduction of E-3" with --reduction of E-3--.

In column 7, line 31, please replace "0°C. in an ice water bath." with --0°C in an ice water bath.--.

In column 7, line 56, please replace "Reduction of E-1" with --Reduction of E-1--.

In column 9, line 14, please replace "Reduction E" with --Reduction of E--.

In column 9, line 39, please replace "0,1338" with -0.133g--.

In column 10, line 40, column 11, line 3, and column 17, line 7, please replace "Reduction of E" with --Reduction of E--.

UNITED STATES PATENT AND TRADEMARK OFFICE
CERTIFICATE OF CORRECTION

PATENT NO. : 5,442,119
DATED : August 15, 1995
INVENTOR(S) : Stephen L. Buchwald and Richard D. Broene It is certified that error appears in the above-indentified patent and that said Letters Patent is hereby corrected as shown below:

In column 11, line 44, please replace "$(L^{iii})(Liv)$" with --$(L^{iii})(L^{iv})$--.

Signed and Sealed this

Second Day of April, 1996

Attest:

BRUCE LEHMAN

Attesting Officer

Commissioner of Patents and Trademarks